US00PP18458P2

(12) United States Plant Patent
Ferguson et al.

(10) Patent No.: US PP18,458 P2
(45) Date of Patent: Jan. 22, 2008

(54) STRAWBERRY PLANT NAMED 'DRISSTRAWONE'

(50) Latin Name: *Fragaria×ananassa*
Varietal Denomination: DrisStrawOne

(75) Inventors: Michael Ferguson, Moorpark, CA (US); Amado Q. Amorao, Camarillo, CA (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 11/545,352

(22) Filed: Oct. 10, 2006

(51) Int. Cl.
*A01H 5/00* (2006.01)

(52) U.S. Cl. ..... Plt./208
(58) Field of Classification Search ..... Plt./208, Plt./209
See application file for complete search history.

*Primary Examiner*—Kent Bell
(74) *Attorney, Agent, or Firm*—Jondle & Associates, P.C.

(57) ABSTRACT

This invention relates to a new and distinct cultivar of strawberry plant named 'DrisStrawOne'. The new cultivar is primarily characterized by its relatively small plant size, medium fruit size and heavy fruit production.

3 Drawing Sheets

Genus and species: *Fragaria×ananassa.*
Variety denomination: 'DrisStrawOne'.

BACKGROUND OF THE NEW PLANT

The present invention relates to a new and distinct strawberry cultivar designated 'DrisStrawOne' botanically known as *Fragaria×ananassa.* This new strawberry cultivar originated from a controlled cross between 'Driscoll El Capitan' (U.S. Plant Pat. No. 14,005) and 'Driscoll Agoura' (U.S. Plant Pat. No. 15,731). The original seedling of the new cultivar was asexually propagated by stolons at a nursery in Shasta County, Calif. Propagules were transplanted to a controlled breeding plot in Ventura County, Calif. where it was identified and selected for further evaluation in February, 2002. 'DrisStrawOne' was subsequently asexually propagated and underwent further testing at various locations in Ventura County, Calif. for four years. The present invention has been found to retain its distinctive characteristics through successive asexual propagations.

DESCRIPTION OF THE PHOTOGRAPHS

The accompanying color photographs show typical specimens of the new cultivar at various stages of development as nearly true as it is possible to make in color reproductions.

DESCRIPTION OF THE NEW CULTIVAR

Figure 1:
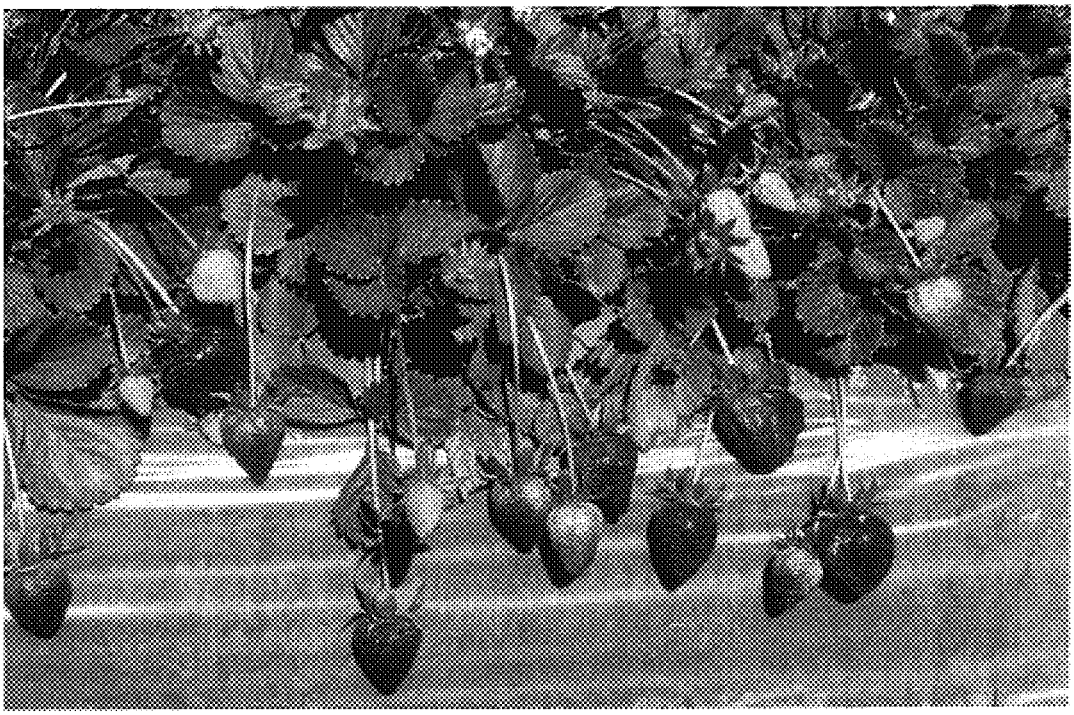
FIG. 1 shows overall plant habit including fruit at various stages of development.
Figure 2:
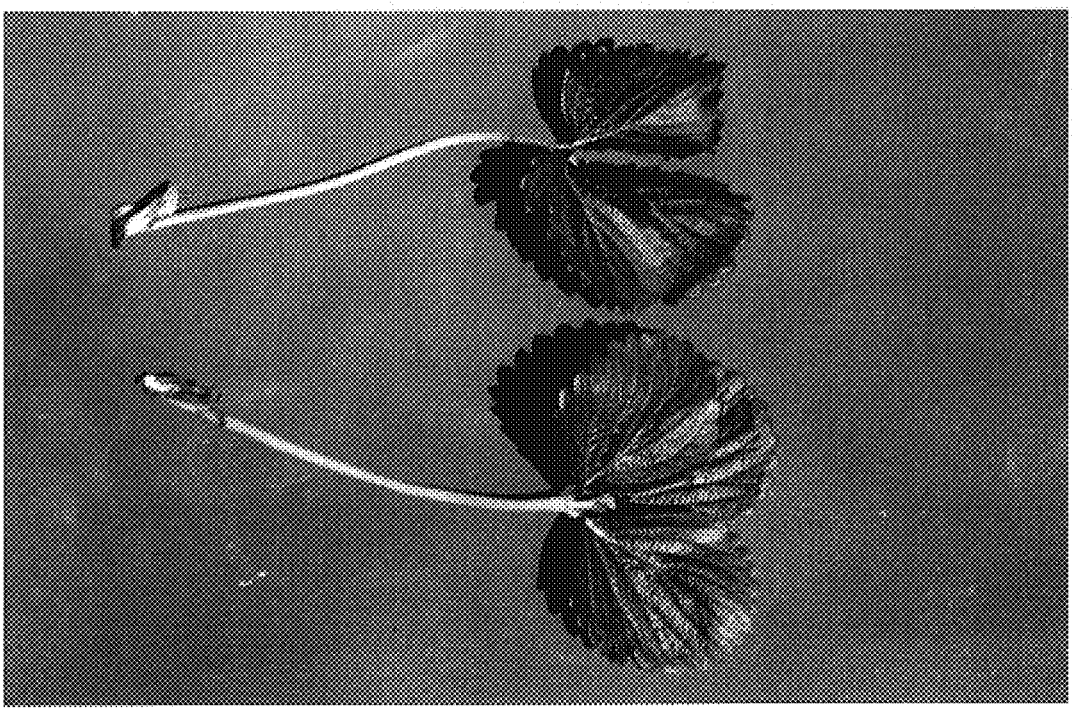
FIG. 2 shows leaves of the plant with three leaflets.
Figure 3:
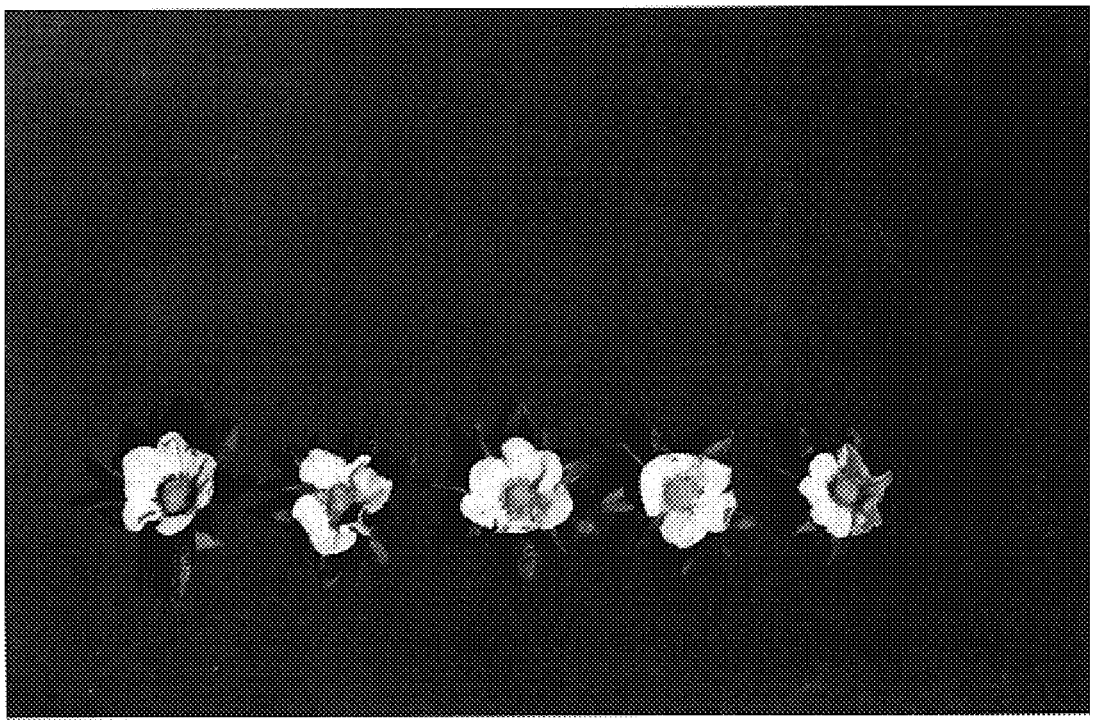
FIG. 3 shows the upperside of the flowers.
Figure 4:
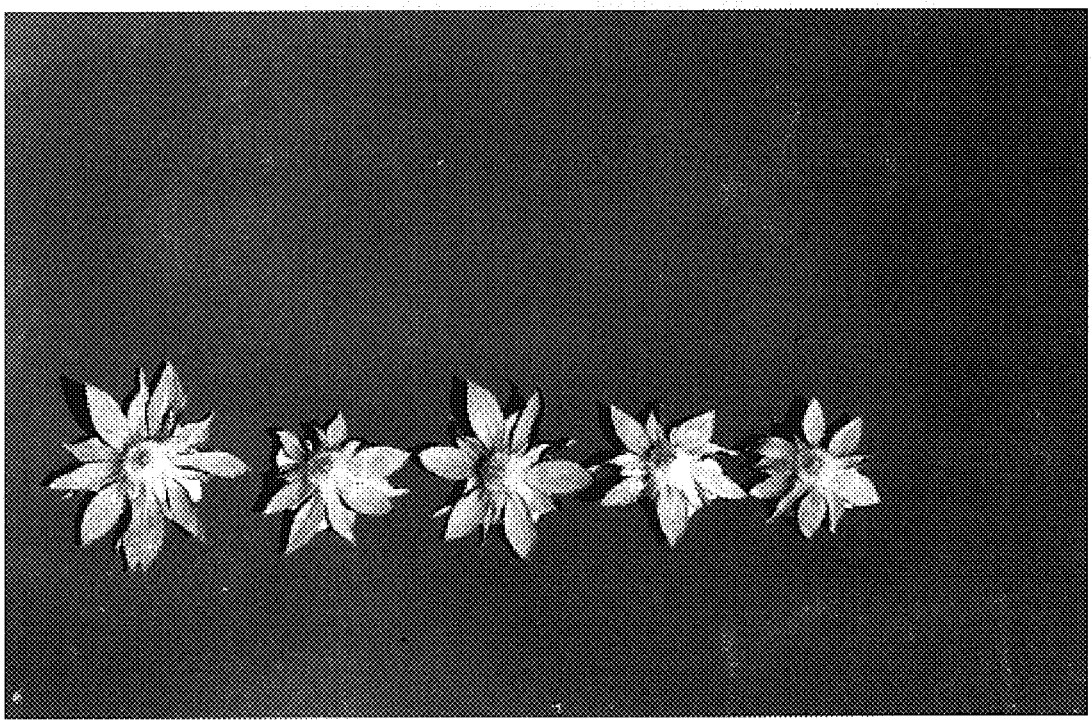
FIG. 4 shows the underside of the flowers.
Figure 5:
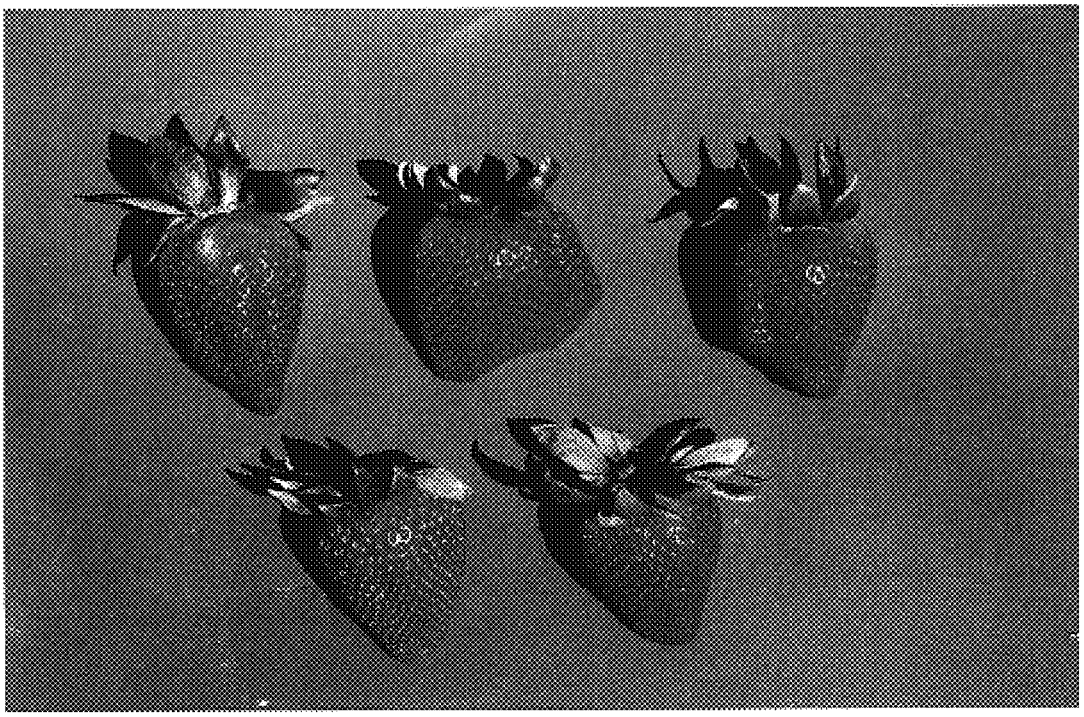
FIG. 5 shows the whole fruit.
Figure 6:
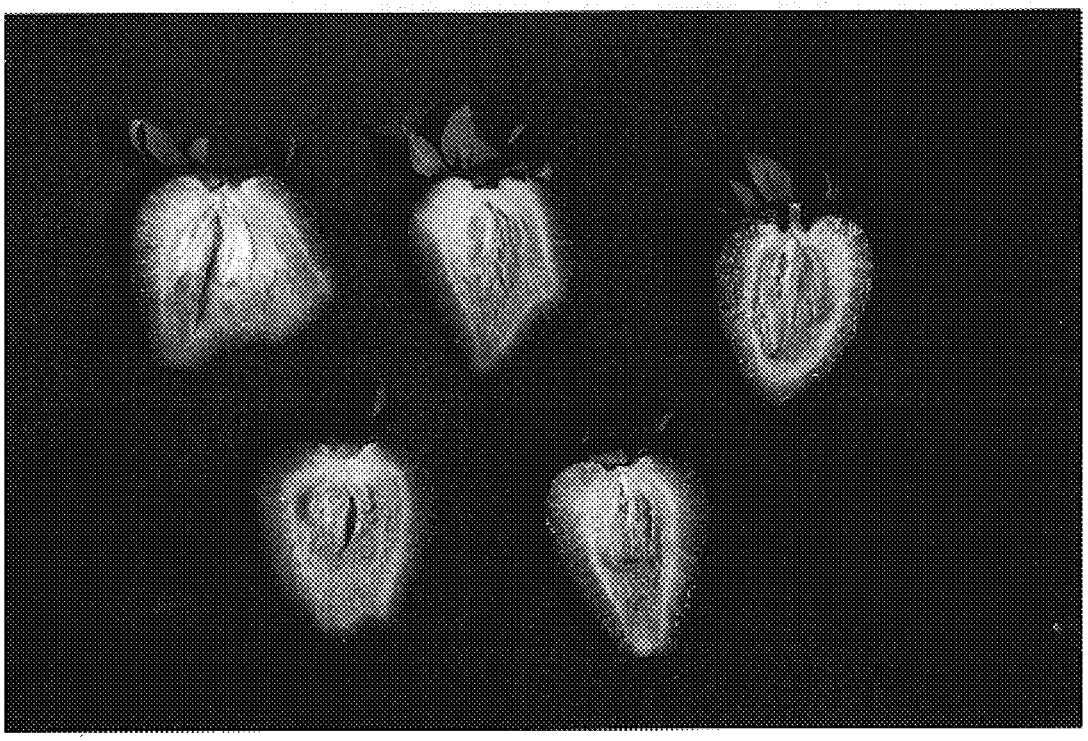
FIG. 6 shows the fruit in longitudinal cross-section.

The following description of 'DrisStrawOne' is based on observations taken during the 2006 growing season in Ventura County, Calif. This description is in accordance with UPOV terminology. Color designations, color descriptions, and other phenotypical descriptions may deviate from the stated values and descriptions depending upon variation in environmental, seasonal, climatic and cultural conditions. 'DrisStrawOne' has not been observed under all possible environmental conditions. Color terminology follows The Royal Horticultural Society Colour Chart, London.

DETAILED BOTANICAL DESCRIPTION

Table 1 shows plant characteristics of the new variety compared with plant characteristics of the parents, 'Driscoll El Capitan' and 'Driscoll Agoura'. Plant characteristics include plant habit, vigor, height in centimeters, diameter in centimeters, the density of an individual plant and the number of crowns per plant.

TABLE 1

| Characteristic | 'DrisStrawOne' | 'Driscoll El Capitan' | 'Driscoll Agoura' |
|---|---|---|---|
| Habit | Upright | Globose | Flat Globose |
| Vigor | Strong | Strong | Weak |
| Height (cm) | 9.5 | 20.2 | 22.9 |
| Diameter (cm) | 15.9 | 35.8 | 30.2 |
| Plant Density | Open | Open | Open |
| No. Crowns/Plant | 5 | 5 | 6 |

Table 2 shows leaf characteristics of the new cultivar compared with leaf characteristics of 'Driscoll El Capitan' and 'Driscoll Agoura'. Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, shape of leaf margin and shape of leaf base.

TABLE 2

| Leaf Characteristic | 'DrisStrawOne' | 'Driscoll El Capitan' | 'Driscoll Agoura' |
|---|---|---|---|
| Terminal leaflet length (cm) | 7.37 | 6.45 | 5.90 |

TABLE 2-continued

| Leaf Characteristic | 'DrisStrawOne' | 'Driscoll El Capitan' | 'Driscoll Agoura' |
|---|---|---|---|
| Terminal leaflet width (cm) | 6.84 | 5.89 | 5.63 |
| Terminal leaflet length/width ratio | 1.08 | 1.10 | 1.05 |
| No. teeth/terminal leaflet | 22 | 18 | 22 |
| Shape of teeth | Rounded | Obtuse | Rounded |
| Color of upperside of leaf | RHS 139A Light green | RHS 147A Dark green | RHS 147A Dark green |
| Color of underside of leaf | RHS 138A Light green | RHS 147C Medium green | RHS 138B Light green |
| Leaf shape in cross section | Concave | Slightly concave | Between slightly concave & flat |
| Leaf blistering | Weak | Medium | Strong |
| Leaf glossiness | Weak | Between medium & strong | Medium |
| No. leaflets | More than 3 leaflets on up to 5 out of 10 leaves | Three only | More than 3 leaflets on up to 5 out of 10 leaves |
| Terminal leaflet margin | Revolute | Flat | Flat |
| Terminal leaflet base shape | Slightly oblique | Obtuse | Rounded |

Table 3 shows information about the petiole, the petiolule, the bract, and the stipule of the new cultivar compared to 'Driscoll El Capitan' and 'Driscoll Agoura'. This includes petiole length in centimeters, petiole diameter in centimeters, petiolule length in centimeters, petiolule diameter in centimeters, bract frequency per petiole, stipule length in centimeters, stipule width in centimeters, stipule pubescence, petiole pubescence, pose of hairs on the petiole, color of the petiole and color of the petiolule.

TABLE 3

| Characteristic | 'DrisStrawOne' | 'Driscoll El Capitan' | 'Driscoll Agoura' |
|---|---|---|---|
| Petiole length (cm) | 12.5 | 10.8 | 10.4 |
| Petiole diameter (cm) | 0.385 | 0.330 | 0.357 |
| Petiole pubescence | Dense | Between medium & dense | Dense |
| Petiole pose of hairs | Between upwards & outwards | Outwards | Outwards |
| Petiole color | RHS 144A Medium yellow green | RHS 149A Light yellow green | RHS 149A Light yellow green |
| Petiolule color | RHS 144B Medium yellow green | | |
| Petiolule length (cm) | 0.770 | 0.518 | 0.320 |
| Petiolule diameter (cm) | 0.264 | 0.194 | 0.221 |
| Bract frequency | 1 | 0 | 0 |
| Stipule length (cm) | 4.0 | 3.9 | 3.8 |
| Stipule width (cm) | 0.965 | 0.939 | 1.123 |
| Stipule pubescence | Dense | Sparse | Sparse |

Table 4 shows stolon characteristics of the new cultivar compared to 'Driscoll El Capitan' and 'Driscoll Agoura'. These characteristics include the number of stolons, the anthocyanin coloration of the stolons, the thickness of the stolons and the pubescence of the stolons.

TABLE 4

| Characteristic | 'DrisStrawOne' | 'Driscoll El Capitan' | 'Driscoll Agoura' |
|---|---|---|---|
| Stolon Number | Medium | Many | Medium |
| Stolon Anthocyanin | Weak | Between Medium & Strong | Between Weak & Medium |
| Stolon Thickness | Medium | Thin | Between Medium & Thick |
| Stolon Pubescence | Sparse | Between Sparse & Medium | Dense |
| Average Number of Daughter Plants (Nursery Average) | 9 | 10 | 11 |

Table 5 shows inflorescence characteristics of the new cultivar compared to 'Driscoll El Capitan' and 'Driscoll Agoura'. These characteristics include inflorescence position relative to foliage, relative flower size, flower diameter in centimeters (measured from petal tip to petal tip), relative spacing of petals, petal length in centimeters, petal width in centimeters, petal length to width ratio, petal color, calyx diameter in centimeters (measured on back off lower from sepal tip to sepal tip), diameter of calyx relative to corolla, diameter of inner calyx relative to outer, sepal length in centimeters (measured from sepal tip to point of attachment to receptacle), sepal width in centimeters, receptacle color and anther color.

TABLE 5

| Characteristic | 'DrisStrawOne' | 'Driscoll El Capitan' | 'Driscoll Agoura' |
|---|---|---|---|
| Inflorescence position relative to foliage | Above | Above | Above |
| Flower size | Medium | Large | Between medium & large |
| Flower diameter (cm) | 2.682 | 3.052 | 2.291 |
| Petal spacing | Overlapping | Overlapping | Overlapping |
| Petal length (cm) | 1.536 | 1.521 | 1.368 |
| Petal width (cm) | 1.429 | 1.607 | 1.274 |
| Petal length/width ratio | 1.07 | 0.95 | 1.07 |
| Petal color | RHS 155D White | RHS 155C White | RHS 155C White |
| Calyx diameter (cm) | 3.924 | 4.401 | 3.953 |
| Calyx diameter relative to corolla | Larger | Larger | Larger |
| Inner calyx diameter relative to outer | Smaller | Between smaller & same size | Same size |
| Sepal length (cm) | 1.458 | 1.720 | 1.538 |
| Sepal width (cm) | 1.175 | 0.748 | 0.629 |
| Receptacle color | RHS 9A | | |
| Anther color | RHS 14A | | |

Table 6 shows fruit characteristics of the new cultivar compared to 'Driscoll El Capitan' and 'Driscoll Agoura'.

TABLE 6

| Characteristic | 'DrisStrawOne' | 'Driscoll El Capitan' | 'Driscoll Agoura' |
|---|---|---|---|
| Fruiting truss length (cm) | 24.4 | 20.9 | 17.7 |
| Fruiting truss attitude | Semi-erect | Prostrate | Flat |
| Fruit length (cm) | 0.538 | 0.414 | 0.463 |

TABLE 6-continued

| Characteristic | 'DrisStrawOne' | 'Driscoll El Capitan' | 'Driscoll Agoura' |
|---|---|---|---|
| Fruit width (cm) | 0.452 | 0.351 | 0.421 |
| Fruit length/width ratio | 1.19 | 1.18 | 1.10 |
| Fruit weight (g) | 29.2 | 27.9 | 28.0 |
| Relative fruit size | Medium | Between medium & large | Between medium & large |
| Predominant fruit shape | Conical | Cordate | Ovoid |
| Difference in shape between primary & secondary fruits | Moderate | Marked | Marked |
| Band without achenes | Absent or very narrow | Absent or very narrow | Absent or very narrow |
| Unevenness of fruit surface | Medium | Between weak & medium | Strong |
| Fruit skin color | RHS 46B Red | RHS 46A Dark red | RHS 46A Dark red |
| Evenness of fruit color | Slightly uneven | Between slightly uneven & even | Slightly uneven |
| Fruit glossiness | Between medium & strong | Strong | Strong |
| Insertion of achenes | Below surface | Between below surface & level with surface | Level with surface |
| Achene coloration - sunward side of berry | RHS 180B Medium greyed red | RHS 183B Dark greyed red | RHS 182A Dark greyed red |

TABLE 6-continued

| Characteristic | 'DrisStrawOne' | 'Driscoll El Capitan' | 'Driscoll Agoura' |
|---|---|---|---|
| Achene coloration - shaded side of berry | RHS 1A Light green yellow | RHS 1B Light yellow | RHS 3B Light yellow |
| Achenes per berry | 202 | 101.5 | 385.5 |
| Insertion of calyx | Between in a basin and level | Between in a basin and level | Set above fruit |
| Pose of calyx segments | Reflexed | Reflexed | Reflexed |
| Size of calyx in relation to fruit | Larger | Larger | Between smaller & same size |
| Adherence of calyx | Medium | Strong | Between weak & medium |
| Firmness of flesh | Medium | Firm | Firm |
| Color of flesh | RHS 41B & RHS 155A Orange red & white | RHS 40B & RHS 155C Orange red & white | RHS 41A & RHS 155B Orange red & white |
| Evenness of flesh color | Slightly uneven | Even | Slightly uneven |
| Hollow center | Medium | Large | Medium |
| Sweetness | Medium | Strong | Medium |
| Texture when tasted | Fine | Fine | Medium |
| Grams of fruit/plant | 957.0 | 509.4 | 704.7 |

We claim:

1. A new and distinct cultivar of strawberry plant as described and shown herein.

* * * * *